United States Patent [19]

Omodei-Salè et al.

[11] Patent Number: 4,459,302

[45] Date of Patent: Jul. 10, 1984

[54] ACYL-1H-1,2,4-TRIAZOLE DERIVATIVES

[75] Inventors: Amedeo Omodei-Salè, Voghera; Pietro Consonni, Milan; Giulio Galliani, Monza, all of Italy

[73] Assignee: Gruppo Lepetit, S.p.A., Milano-Bovisa, Italy

[21] Appl. No.: 87,375

[22] Filed: Oct. 23, 1979

[30] Foreign Application Priority Data

Oct. 30, 1978 [GB] United Kingdom ............... 42417/78

[51] Int. Cl.³ .................... A61K 31/41; C07D 249/08
[52] U.S. Cl. .................................... 424/269; 548/262
[58] Field of Search .................. 548/262; 424/269; 542/439, 440

[56] References Cited

U.S. PATENT DOCUMENTS

| | | | |
|---|---|---|---|
| 3,308,131 | 3/1967 | McKusick | 548/262 |
| 4,119,635 | 10/1978 | Omodei-Sale et al. | 548/262 |
| 4,154,841 | 5/1979 | Wade et al. | 548/266 |

FOREIGN PATENT DOCUMENTS 1351430  5/1974  United Kingdom ............... 548/262

OTHER PUBLICATIONS

Kubota et al., Chem. Pharm. Bull., (Japan), vol. 23, pp. 955–966, (1975).

Primary Examiner—Alton D. Rollins
Attorney, Agent, or Firm—Maynard R. Johnson; Ronald G. Brookens; Richard G. Waterman

[57] ABSTRACT

New acyl-1H-1,2,4-triazole derivatives of the formula

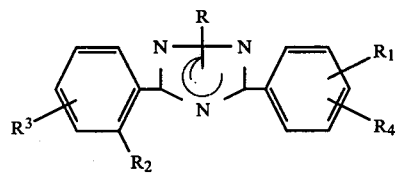

wherein
R may be located on one of the two adjacent nitrogen atoms and may represent hydrogen; a group $R_5$-CO wherein $R_5$ is selected from $(C_{1-4})$alkyl, $(C_{2-4})$alkenyl, $(C_{2-4})$alkynyl, phenyl, phenyl substituted by one to three groups independently selected from halo, $(C_{1-4})$alkyl, $(C_{1-4})$alkoxy, trifluoromethyl, cyano, nitro, amino, di-$(C_{1-4})$alkylamino, $(C_{2-4})$acylamino and methylenedioxy, benzyl, cinnamyl, amino, $(C_{1-4})$alkylamino, di-$(C_1$-$C_4)$alkylamino, phenylamino, phenylamino wherein the phenyl ring may be substituted by one to three groups independently selected from halo, $(C_{1-4})$alkyl, $(C_{1-4})$alkoxy, trifluoromethyl, cyano, nitro, amino, di-$(C_{1-4})$alkylamino, $(C_{2-4})$acylamino and methylenedioxy, halo$(C_{1-4})$alkyl, $(C_{1-4})$alkoxy and benzyloxy;

a group $R_6$-$SO_2$ wherein $R_6$ may represent $(C_{1-4})$alkyl, phenyl, phenyl substituted by a radical selected from $(C_{1-4})$alkyl and $(C_{1-4})$alkoxy, or phenacyl;

$R_1$ is selected from hydrogen, $(C_{1-4})$alkyl, $(C_{1-4})$alkoxy, allyloxy, propargyloxy, trifluoromethyl, phenyl, halo and dimethylamino;

$R_2$ may represent a $(C_{1-4})$alkyl radical or the group

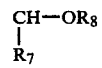

wherein $R_7$ is hydrogen or methyl and $R_8$ is a $(C_{1-4})$alkyl radical, the group $R_5$-CO or the group $R_6$-$SO_2$ in which $R_5$ and $R_6$ are defined as above, or $R_7$ and $R_8$ taken together may represent a further bond between the carbon and oxygen atom;

$R_3$ and $R_4$ are independently selected from hydrogen, halo, $(C_{1-4})$alkyl and $(C_{1-4})$alkoxy;

$R_1$ and $R_4$ taken together may also represent a methylenedioxy group; with the proviso that, when R represents hydrogen, $R_2$ must be the group

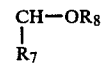

in which $R_8$ must be the group $R_5$-CO or the group $R_6$-$SO_2$ wherein $R_5$ and $R_6$ are as above defined;

and salts therewith of pharmaceutically acceptable acids. The compounds possess antireproductive utility.

11 Claims, No Drawings

ACYL-1H-1,2,4-TRIAZOLE DERIVATIVES

BACKGROUND OF THE INVENTION 3,5-Disubstituted 1,2,4-triazoles wherein the substituents at the 3 and 5 positions are phenyl moieties are known from the chemical literature, see for instance K. T. Potts, Jour. Chem.Soc.3461, 1954; D. L. Liljégren et al., Jour.Chem.Soc., 518, 1901 and C.A. 85, 123931 s, 1976, but those where one of the two substituents at the 3 and 5 positions is a 2-acyloxymethyl-phenyl group are new. On the other hand, 3,5-di-substituted 1,2,4-triazoles having also an acyl group on one of the two adjacent nitrogen atoms are a class of compounds which have been scarcely investigated. The literature describes the chemico-physical properties of the 1-acetyl-3,5-diphenyl-1,2,4-triazole and the 1-acetyl-3-phenyl-5-(4-methylphenyl)-1H-1,2,4-triazole (see again K. T. Potts, Jour. Chem. Soc. 3461, 1954).

SUMMARY OF THE INVENTION

The present invention relates to new acyl-1H-1,2,4-triazole derivatives having anti-reproductive utility, to the process for their manufacture and to their use an antireproductive agents. More particularly, the present invention relates to new acyl-1H-1,2,4-triazole derivatives of formula

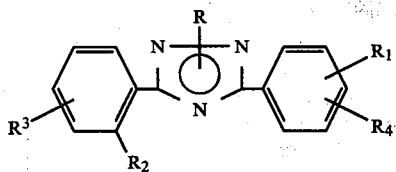

wherein:

R may be located on one of the adjacent nitrogen atoms and may represent hydrogen; a group $R_5$—CO wherein $R_5$ is selected from $(C_{1-4})$alkyl, $(C_{2-4})$alkenyl, $(C_{2-4})$alkynyl, phenyl, phenyl substituted by one to three groups independently selected from halo, $(C_{1-4})$alkyl, $(C_{1-4})$alkoxy, trifluoromethyl, cyano, nitro, amino, di-$(C_{1-4})$alkylamino, $(C_{2-4})$acylamino and methylenedioxy, benzyl, cinnamyl, amino, $(C_{1-4})$alkylamino, di-$(C_{1-4})$alkylamino, phenylamino, phenylamino wherein the phenyl ring may be substituted by one to three groups independently selected from halo, $(C_{1-4})$alkyl, $(C_{1-4})$alkoxy, trifluoromethyl, cyano, nitro, amino, di-$(C_{1-4})$alkylamino, $(C_{2-4})$acylamino and methylenedioxy, halo$(C_{1-4})$alkyl, $(C_{1-4})$alkoxy and benzyloxy; a group $R_6$—$SO_2$ wherein $R_6$ may represent $(C_{1-4})$alkyl, phenyl, phenyl substituted by a radical selected from $(C_{1-4})$alkyl and $(C_{1-4})$alkoxy, or phenacyl;

$R_1$ is selected from hydrogen, $(C_{1-4})$alkyl, $(C_{1-4})$alkoxy, allyloxy, propargyloxy, trifluoromethyl, phenyl, halo and dimethylamino;

$R_2$ may represent a $(C_{1-4})$alkyl radical or the group

wherein $R_7$ is hydrogen or methyl and $R_8$ is a $(C_{1-4})$alkyl radical, the group $R_5$—CO or the group $R_6$—$SO_2$ in which $R_5$ and $R_6$ are defined as above, or $R_7$ and $R_8$ taken together may represent a further bond between the carbon and oxygen atom; $R_3$ and $R_4$ are independently selected from hydrogen, halo, $(C_{1-4})$alkyl and $(C_{1-4})$alkoxy;

$R_1$ and $R_4$ taken together may also represent a methylenedioxy group; with the proviso that, when R represents hydrogen, $R_2$ must be the group

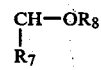

in which $R_8$ must be the group $R_5$—CO or the group $R_6$—$SO_2$ wherein $R_5$ and $R_6$ are as above defined; and salts therewith of pharmaceutically acceptable acids. As used herein, the terms "$(C_{1-4})$alkyl" and "$(C_{1-4})$alkoxy" designate linear or branched alkyl and alkoxy radicals containing from 1 to 4 carbon atoms. The terms "$(C_{2-4})$alkenyl" and "$(C_{2-4})$alkynyl" designate hydrocarbon rests of 2 to 4 carbon atoms with one double bond or one triple bond respectively.

The term "$(C_{2-4})$acylamino" designates groups selected from acetylamino, propionylamino, butyrylamino and isobutyrylamino. The term "halo" is intended to indicate essentially chlorine, fluorine and bromine.

A preferred group of compounds comprises those compounds of formula I wherein R may be located on one of the two adjacent nitrogen atoms and represents hydrogen or the group $R_5$—CO in which $R_5$ is selected from $(C_{1-4})$alkyl, phenyl, phenyl substituted by a radical selected from halo, $(C_{1-4})$alkyl, $(C_{1-4})$alkoxy and nitro, amino, $(C_{1-4})$alkylamino, di-$(C_{1-4})$-alkylamino, phenylamino, phenylamino wherein the phenyl ring is substituted by a group selected from halo, $(C_{1-4})$alkyl, $(C_{1-4})$alkoxy and nitro, and $(C_{1-4})$alkoxy; $R_1$ is selected from $(C_{1-4})$alkoxy, allyloxy, propargyloxy and halo; $R_2$ may represent a $(C_{1-4})$alkyl radical or the group

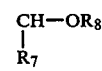

in which $R_7$ is hydrogen and $R_8$ is the group $R_5$—CO wherein $R_5$ is defined in this preferred group; $R_3$ and $R_4$ are independently selected from hydrogen, halo and $(C_{1-4})$ alkoxy; with the proviso that when R is hydrogen, $R_2$ must be the group

in which $R_7$ must be hydrogen and $R_8$ the group $R_5$—CO in which $R_5$ is as defined in this preferred group; and salts therewith of pharmaceutically acceptable acids. A second preferred group of compounds comprises those compounds of formula I wherein R may be located on one of the two adjacent nitrogen atoms and represents hydrogen or the group $R_5$—CO in which $R_5$ is selected from $(C_{1-4})$alkyl, phenyl, amino, $(C_{1-4})$alkylamino, di-$(C_{1-4})$alkylamino, phenylamino, phenylamino wherein the phenyl ring is substituted by a group selected from halo, $(C_{1-4})$alkyl, $(C_{1-4})$alkoxy and nitro; $R_1$ represents halo or $(C_{1-4})$alkoxy; $R_2$ is a $(C_{1-4})$alkyl radical or the group

in which $R_7$ is hydrogen and $R_8$ represents $R_5$—CO wherein $R_5$ is as defined in this preferred group; $R_3$ and $R_4$ are independently selected from hydrogen, halo and $(C_{1-4})$alkoxy; with the proviso that, when $R_1$ is hydrogen, $R_2$ must be the group

in which $R_7$ is hydrogen and $R_8$ represents $R_5$—CO in which $R_5$ is as defined in this preferred groups and salts therewith of pharmaceutically acceptable acids.

A most preferred group of compounds comprises those compounds of formula I wherein R may be located on one of the two adjacent nitrogen atoms and represents the group $R_5$—CO wherein $R_5$ is selected from $(C_{1-4})$alkyl, phenyl, amino, methylamino, ethylamino, dimethylamino, diethylamino, phenylamino, phenylamino in which the phenyl ring is substituted by a group selected from methyl, ethyl, methoxy, ethoxy, fluoro, chloro and nitro, and $(C_{1-4})$alkoxy; $R_1$ represents chloro, fluoro, methoxy or ethoxy; $R_2$ represents a $(C_{1-4})$alkyl radical; $R_3$ may be hydrogen, fluoro, chloro, methoxy or ethoxy; and $R_4$ is hydrogen and salts therewith of pharmaceutically acceptable acids. Pharmacologically-acceptable salts include those derived from mineral acids such as hydrochloric acid, hydrobromic acid, sulfuric acid as well as those derived from organic acids such as lactic, maleic, succinic, fumaric, oxalic, glutaric, citric, malic, tartaric, p-toluenesulfonic, benzenesulfonic, methanesulfonic, cyclohexanesulfonic acid and the like. They are prepared according to the conventional methods.

The compounds of the invention are prepared by subjecting to common acylation procedures a 3,5-disubstituted 1H-1,2,4-triazole of the following formula

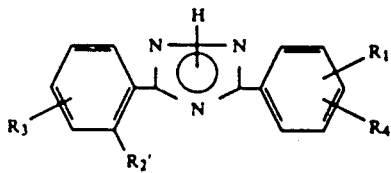

wherein $R_1$, $R_3$ and $R_4$ are defined as above and $R'_2$ is a $(C_{1-4})$alkyl radical or the group

in which $R_7$ is defined as above and $R_8'$ may be hydrogen or $(C_{1-4})$alkyl, or $R_7$ and $R_8'$ taken together may represent a further bond between the carbon and the oxygen atoms. Thus, a general method for preparing the compounds of formula I in which R is either the group $R_5$—CO or the group $R_6$—SO$_2$ comprises reacting a molar proportion of a triazole of formula II with an about equimolecular proportion of an acylating agent of formula $R_5$—CO X or $R_6$—SO$_2$ X, wherein $R_5$ and $R_6$ are defined as above and X is a halogen atom, preferably chlorine, or the 1-imidazolyl radical.

The reaction is carried out in the presence of an acid binding agent e.g. a tertiary organic nitrogen containing base such as, for instance, trimethylamine, triethylamine, pyridine, pycoline, collidine and analogs, at a temperature which may vary from room temperature to the reflux temperature of the reaction mixture. The reaction may run both in the absence and in the presence of an organic solvent. If employed, preferred organic solvents are selected from benzene, dioxane, tetrahydrofuran, 1,2-dichloroethane, and analogs. It has also been observed that the tertiary base may act as the solvent as well.

The use of the tertiary organic nitrogen containing base is avoided if the condensation is carried out by using as the triazole substrate the salt of a triazole of formula II with an alkali metal. To this purpose a molar proportion of the selected substance of formula II is treated in an anhydrous inert organic solvent, e.g. benzene, dioxane and, preferably, tetrahydrofuran, under an inert gas atmosphere, e.g. nitrogen or argon, with an equimolecular proportion of an alkali hydride (suspension in mineral oil), e.g. sodium hydride or potassium hydride or a metallating agent like butyl-lithium or a Grignard reagent. The so obtained alkali salt is generally not isolated but is allowed to react with an equimolecular amount (calculated over the starting triazole) of the selected acyl chloride of formula $R_5$—CO X or $R_6$—SO$_2$X, wherein $R_5$, $R_6$ and X are defined as above. The reaction is completed with a period of time varying from about 2 to about 30 hours, at a temperature which is preferably the room temperature. A gentle heating may sometimes be applied in order to speed up the acylation procedure. This procedure is especially adopted when compounds of formula I are desired wherein R is the group $R_5$—CO in which $R_5$ represents phenyl, phenyl substituted as above defined, benzyl, cinnamyl, di-$(C_{1-4})$alkylamino, $(C_{1-4})$alkoxy or benzyloxy. A convenient way for preparing compounds of formula I wherein R is the radical $R_5$—CO in which $R_5$ represents $(C_{1-4})$alkyl, $(C_{2-4})$alkenyl, $(C_{2-4})$alkynyl, phenyl, phenyl substituted as above defined, cinnamyl, and halo$(C_{1-4})$alkyl such as chloromethyl, dichloromethyl and trifluoromethyl, comprises reacting a triazole of formula II with an anhydride of formula $(R_5$—CO$)$—O—Y wherein $R_5$ represents $(C_{1-4})$alkyl, $(C_{2-4})$alkenyl, $(C_{2-4})$alkynyl, benzyl, phenyl, phenyl substituted as above defined, cinnamyl and halo$(C_{1-4})$alkyl, and Y may be the same group $R_5$—CO in which $R_5$ represents $(C_{1-4})$alkyl, $(C_{2-4})$alkenyl, $(C_{2-4})$alkynyl, benzyl, phenyl, phenyl substituted as above defined, cinnamyl, halo$(C_{1-4})$alkyl, or $(C_{1-4})$alkoxy. In the actual practice a molar proportion of a predetermined triazole of formula II is contacted with 1-3 molar equivalents of an anhydride of formula $(R_5$—CO$)$—O—Y wherein $R_5$ represents $(C_{1-4})$alkyl, $(C_{2-4})$alkenyl, $(C_{2-4})$alkynyl, benzyl, phenyl, phenyl substituted as above defined, cinnamyl, and halo$(C_{1-4})$alkyl, and Y has the previously indicated meanings.

The presence of a solvent is not strictly necessary and depends on the nature of the two reaction partners. When a solvent is employed, it is generally selected from anhydrous inert organic solvents, e.g. benzene, toluene, methylene chloride, dioxane, tetrahydrofuran or a mixture thereof. The reaction is carried out preferably at the boiling temperature of the reaction mixture even though is has been found that it runs satisfactorily also at room temperature. Generally, from about 2 to about 25 hours are required for having the reaction completed. A useful method for preparing the compounds of formula I wherein R is the group $R_5$—CO in which $R_5$ is amino, $(C_{1-4})$alkylamino, phenylamino or phenylamino wherein the phenyl ring may be substituted as above defined comprises reacting the triazole substrate of formula II with an alkali isocyanate, a $(C_{1-4})$alkylisocyanate or a phenylisocyanate wherein the phenyl ring may also be substituted by one to three groups independently selected from halo, $(C_{1-4})$alkyl, $(C_{1-4})$alkoxy, trifluoromethyl, cyano, nitro, amino, di-$(C_{1-4})$alkylamino, $(C_{2-4})$acylamino or a group methylene dioxy. In the actual practice, the reaction is carried out by contacting the reactants in substantially equimolecular amounts, optionally in the presence of an organic solvent such as, for instance, benzene, methylene chloride, ethyl acetate, acetonitrile and analogs, at a temperature which is comprised between room temperature and the reflux temperature of the reaction mixture. The reaction is then completed within a period of time varying from about 3 to about 20 hours.

It will result clear to any person skilled in the art that when a triazole of formula II is used as the starting material wherein $R_2'$ is the radical

in which $R_8'$ is hydrogen, the resulting group CH—OH may be involved in the same acylation reaction above illustrated. Thus, compounds of formula I may be obtained wherein $R_2$ represents the group

in which $R_8$ stands for $R_5$—CO or $R_6$—$SO_2$, having $R_5$ and $R_6$ the same meanings as above. If this occurs, the acyl group introduced on to one of the two adjacent nitrogen atoms of the triazole ring is the same acyl group which has replaced the hydrogen atom of the group

If desired, these compounds may be subjected to a mild alkaline hydrolysis, thus obtaining compounds of formula I wherein R is hydrogen, $R_1$, $R_3$ and $R_4$ are as above defined and $R_2$ is the group

in which $R_7$ has the previously reported meanings and $R_8$ represents $R_5$—CO or $R_6$—$SO_2$, being $R_5$ and $R_6$ defined as above.

In the actual practice, the hydrolysis is carried out by contacting a molar proportion of the predetermined triazole substrate with about two molar equivalents of a mild alkaline agent, e.g. diluted aqueous sodium or potassium bicarbonate, in the presence of an organic solvent, e.g. dioxane, tetrahydrofuran and analogs, at a temperature comprised between about room temperature and the boiling temperature of the reaction mixture.

The hydrolysis is completed within a period of time varying from about 5 to about 20 hours. Finally, it was observed that the compounds of formula I wherein R is on the nitrogen atom of the triazole ring adjacent to the carbon atom bearing the substituent

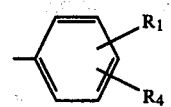

and represents amino, $(C_{1-4})$alkylamino, di-$(C_{1-4})$alkylamino, phenylamino or phenylamino wherein the phenyl ring may be substituted as above, may undergo a rearrangement according to which the R radical shifts onto the adjacent nitrogen atom. In the actual practice, the rearrangement occurs either by heating a molar amount of a predetermined triazole substrate of formula I wherein R is as herein defined at a temperature comprised between about 80° and about 120° C., or by dissolving the compound in a polar solvent such as for instance, a $(C_{1-3})$aliphatic alcohol, and allowing the solution to stand at room temperature by 3-8 hours. The compounds of formula I obtained by the methods described above are recovered through common procedures which are entirely familiar in the field of the organic chemistry. These procedures comprise bringing to dryness the reaction mixture, taking up the residue with a suitable solvent from which the desired end products crystallize. A further purification by column chromatography or recrystallization from a suitable solvent may be sometimes necessary.

According to what is known from the chemical literature (see Kubota and Uda, Chem. Pharm. Bull. 23 (5), 955, 1975), the 3,5-disubstituted 1,2,4-triazoles of formula II are to be regarded as a mixture of two tautomeric forms, i.e. those in which the hydrogen atom is located on one or the other of the two adjacent nitrogen atoms. For numbering purposes, in the N-unsubstituted triazole the phenyl group

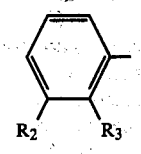

is conventionally assigned the position 5 and the other group

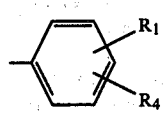

the position 3. At ordinary temperature, these forms are in a state of dynamic equilibrium, i.e. they rapidly exchange into each other, and, depending on the nature of the substituents at the 3 and 5 positions, a form may predominate on the other one. Therefore, it will result clear to any person skilled in the art that, according to the acylation procedures above described, the compounds of formula I wherein R is other than hydrogen may be obtained as single compounds wherein only one of the two adjacent nitrogen atoms has been involved in the acylation reaction, as well as a mixture of the two possible isomers wherein all of the two adjacent nitrogen atoms have been involved in the acylation reaction.

In numbering these N-substituted triazoles, the nitrogen atom bearing the substituent R, is conventionally assigned the number 1 and the adjacent nitrogen atom the number 2. Thus, the carbon atoms bearing the substituents

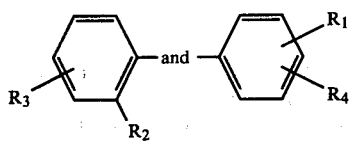

are assigned the numbers 3 or 5 respectively, depending on which of the two adjacent nitrogen atoms bears the substituent R.

The obtainment of single compounds or of mixtures of the two possible isomers depends not only on the nature of the substrate of formula II, but also on the type of the acylating agent and the reaction conditions: however, a general rule can not be established. In any case, if a mixture of isomers, which possesses the same degree of anti-reproductive activity of the single compounds is obtained, this can be separated into the single components by means of known chemico-physical techniques. An example illustrative of the way a mixture can be resolved into the single components is the fractional crystallization, which is based on the different solubilities of the components in a predetermined solvent at different temperatures. Suitable solvents which may be advantageously employed in this method are selected from hexane, ethyl acetate, $(C_{1-4})$alkyl ethers, methylene chloride, light petroleum and mixtures thereof. A further illustrative example is represented by the column chromatography on non-acid, buffered supports, e.g. pH 7 buffered silica-gel. A third illustrative example is represented by the preparative high pressure liquid chromatography (preparative HPLC), which is carried out by employing suitable columns, as an example silica-gel esterified with octylsilane or octadecylsilane. Other obvious procedures useful for resolving a mixture of isomers into the single components are intended to fall within the scopes of the invention. The position of the acyl group on the triazole nucleus was investigated by means of N.M.R. studies. It was based on the observation that the introduction of the acyl group onto the one of the two adjacent nitrogen atoms of the triazole ring was responsible of a variation of the chemical shift (expressed in δ units) of the proton or protons bound to the carbon atom of the radical $R_2$ which is directly connected to the benzene ring with respect to the chemical shift of the same proton or protons on the same carbon atom of the corresponding non-acylated compound. Bearing in mind the meanings of $R_2$, this proton or these protons will hereinafter be referred to as "tolylic proton" or "tolylic protons", whereas the variation of the chemical shift will hereinafter be expressed through the symbol "Δ δ". More particularly it was found that the introduction of the acyl group onto the triazole ring caused, in some instances, a diamagnetic shift (shift toward lower δ values, negative Δ δ) of the "tolylic proton" or "tolylic protons" with respect to the corresponding non-acylated compounds, in other instances a paramagnetic shift (shift toward higher δ values, positive Δ δ).

On the basis of these observations and theoretical considerations on the steric and electronic effects of the acyl substituent, the compounds showing a negative Δ δ were assigned a structure in which the acyl group is on the nitrogen atoms of the two adjacent ones which is connected with the carbon atom bearing the substituent

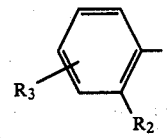

while the compounds showing a positive Δ δ were assigned a structure in which the acyl group is on the other nitrogen atom of the two adjacent ones. These assumptions were confirmed by investigating the same effect on a pair of closely structurally related compounds, namely the 4-phenyl(2-(2-methylphenyl)-1H-imidazole of formula

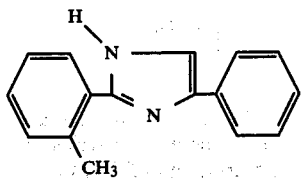

and the 1-acetyl-4-phenyl-2-(2-methylphenyl)-1H-imidazole of formula

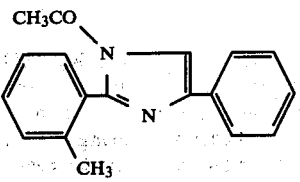

which, as far as the heterocyclic nucleus is concerned, differ from the substances of the present invention only for the substitution of nitrogen atom with a CH group. Compounds III and IV were prepared according to conventional procedures which will be illustrated in the examples. The comparison of the N.M.R. spectra of III and IV confirmed the above assumption ie, the introduction of the acetyl group in the position shown in formula IV caused a negative Δ δ of the protons of the underlined methyl group with respect to the non-acetylated imidazole of formula III. Bearing in mind the statement before mentioned it derives also that the compounds of formula I wherein R is hydrogen, $R_1$, $R_3$ and $R_4$ are as above defined and $R_2$ is the group

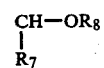

wherein $R_7$ is hydrogen or methyl and $R_8$ is the group $R_5$—CO or $R_6$—$SO_2$, being $R_5$ and $R_6$ as above defined may exist in two tautomeric forms wherein the hydrogen atom is located on one or the other of the two adjacent nitrogen atoms of the triazole ring. Both forms have to be considered as a part of the invention. Anyhow, in these last compounds, for numbering purposes, the phenyl group

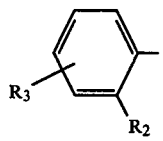

is considered to be at the 5-position and the other phenyl group at the 3-position.

As stated above, the compounds of the present invention display very interesting anti-reproductive utility. More particularly, they show a remarkable post-coital post-implantation anti-reproductive action when administered by different pharmacological routes to laboratory animals, e.g. rats, hamsters, dogs, monkeys and baboons. Moreover, the antifertility activity of these new compounds is not associated with other biological effects which are usual with hormonal substances. The use of the novel acyl-1H-1,2,4-triazole as anti-reproductive agents refers to all industrially applicable aspects and acts of said use, including the embodying of the novel compounds into pharmaceutical compositions. The pharmaceutical compositions containing said active compounds are in fact a further specific object of this invention.

Fertility regulation can usually be achieved in a number of ways through the administration of hormonal substances. These can involve ovulation inhibition, ova transport, fertilization, implantation of the zygote, resorption of the fetus or abortion. Only with ovulation inhibition has there developed a successful method that is clinically useful. The compounds of this invention allow an entirely new approach to this problem in which a non-hormonal compound can be administered parenterally, orally or by intravaginal route once or more times as needed after a "missed period" or to induce termination of a more advanced pregnancy. Representative experiments for assessing antifertility activity were carried out with female Syrian golden hamsters weighing 100 to 130 g. The animals were mated and the presence of sperm in the vagina was taken as evidence of mating. The day sperm was detected and considered day one of pregnancy, since in our laboratories and those of other investigators 90 to 100% of animals that mate as evidenced by vaginal sperm are pregnant.

Pregnancy was later confirmed at the time of autopsy by presence of fetuses or implantation sites in the uterus. Even if an animal aborts the fetus, implantation scars still remain as evidence that the animal has been pregnant. The compounds of the invention, which possess a high solubility in the commonly employed pharmaceutical vehicles, were dissolved in sesame oil containing 20% of benzyl benzoate and administered subcutaneously in doses of 10 mg/kg daily for 5 days beginning on day 4 of pregnancy (days 4–8). The animals were autopsied on day 14 of pregnancy and the uteri were examined for evidence of pregnancy (implantation sites, fetalresorption or live fetuses), hemorrhage, and evidence of abnormalities of the uterus, placenta or fetuses. A compound was considered to be active if there was a reduction of live fetuses in at least 60% of the treated animals and the presence of implantation sites proves the animal to have been pregnant. The compounds of the invention proved to be active according to the above-mentioned criteria, whereas a structurally related compound, namely the 1-methyl-3-(3-methoxyphenyl)-5-(2-(methylphenyl)-1H-1,2,4-triazole of formula

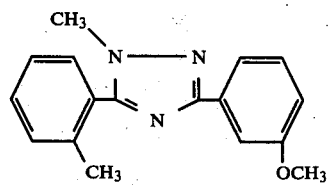

(see Example 38 of GB P. 1, 351, 430) proved to be much less active.

The compounds were then studied for dose-activity relationship and the corresponding $ED_{50}$ values, i.e. 100% activity (absence of live fetuses) in 50% of the animals, were also detrmined. The following Table reports the $ED_{50}$ values of some representative compounds of the invention as well as that of the above mentioned known substance:

TABLE 1

| Compound of Example | $ED_{50}$ mg/kg s.c. hamster |
|---|---|
| 1 | 0.05 |
| 2 | 0.07 |
| 3 | 0.15 |
| 5 | 0.06 |
| 6 | 0.04 |
| 7 | 0.04 |
| 8 | 0.05 |
| 9 | 0.05 |
| 10 | 0.06 |
| 11 | 0.1 |
| 13 | 0.05 |
| 14 | 0.15 |
| 15 | 0.05 |
| 16 | 0.05 |
| 17 | 0.07 |
| 18 | 0.05 |
| 19 | 0.05 |
| 20 | 0.05 |
| 21a | 0.05 |
| 21b | 0.04 |
| 22a | 0.08 |
| 22b | 0.08 |
| 24 | 0.04 |
| 1-Methyl-3-(3-methoxyphenyl)-5-(2-methylphenyl)-1H-1,2,4,-triazole | >10 |

>more than

The same criteria and experimental conditions as above were also applied when the anti-reproductive activity of the compounds of the invention was investigated in other animal species such as, for instance, rats, dogs, monkeys and baboons. In representative experiments, female Sprague-Dawley rats weighing from 200 to 300 g. were treated subcutaneously with a dosage of 20 mg/kg of the compound to be tested, dissolved in sesame oil containing 20% of benzyl benzoate, for five consecutive days starting from day 6 of pregnancy. The rats were killed and autopsied on day 16 and the uteri were examined as seen above for hamsters. Also in this experiment the compounds of the invention caused a reduction of live fetuses in at least 60% of the treated rats. Favorable results were also obtained by administering the compounds of the invention by oral and vaginal routes. The experiments for assessing these properties were carried out on hamsters following the same procedures as above, with the obvious exception that the compounds were administered orally or intravaginally instead of subcutaneously.

The reduction of about 60% of live fetuses was observed at an oral dosage of 10 mg/kg. The oral $ED_{50}$ value was found to range from about 1 to about 5 mg/kg.

Finally, the compounds of the invention display a very low toxicity. In fact, their $LD_{50}$-values, determined according to Lichtfield and Wilcoxon, Journ. Pharm. Expt. Ther., 96, 99, 1949, are never lower than 600 mg/kg when administered to mice by intraperitoneal route.

The facts that the compounds of the invention possess an outstanding anti-reproductive activity even when administered by oral route and are very soluble in the common pharmaceutical carriers represent undoubtedly further important properties. As an example, the high solubility causes the compounds to be readily absorbable and incorporable into suitable and more tolerable injectable dosage forms which possess less drawbacks than corresponding forms wherein the active ingredient is suspended in the carrier. On the other hand, also the activity by oral or intravaginal route allows the compounds to be embodied into more acceptable pharmaceutical preparations.

It results, therefore, that the compounds of the invention may be administered by various routes: orally, subcutaneously, intramuscularly or intravaginally.

For oral administration the substances are compounded in such forms as tablets, dispersible powders, capsules, granules, syrups, elixirs and solutions.

The compositions for oral use may contain one or more conventional adjuvants, such as, for instance, sweetening agents, coloring agents, coating and preservative agents, in order to provide an elegant and palatable preparation. Tablets may contain the active ingredient admixed with conventional, pharmaceutically acceptable excipients, e.g. inert diluents, such as calcium carbonate, sodium carbonate, lactose and talc, granulating and disintegrating agents, such as, for instance, starch, alginic acid and sodium carboxymethylcellulose, binding agents, e.g. starch, gelatin, gumarabic and polyvinylpyrrolidone and lubricating agents, e.g. magnesium stearate, stearic acid and talc.

Syrups, elixirs and solutions are formulated as known in the art. Together with the active compound they may contain suspending agents, such as, for instance, methylcellulose, hydroxyethylcellulose, tragacanth and sodium alginate, wetting agents, e.g. lecithin, polyoxyethylene stearates and polyoxyethylene sorbitan monooleate, and the common preservative, sweetening and buffering agents. A capsule or a tablet may contain the active ingredient alone or admixed with an inert solid diluent, such as, for instance, calcium carbonate, calcium phosphate and kaolin.

Besided the oral route, other useful ways for administering the compounds of the invention may be suitably employed, such as, for instance, the subcutaneous or the intramuscular administration.

The active ingredient is thus embodied into injectable dosage forms. Such compositions are formulated according to the art and may contain appropriate dispersing or wetting agents and suspending or buffering agents identical or similar to those mentioned above.

Sesame oil, benzyl alcohol, benzyl benzoate, peanut oil and their mixtures may also be suitably employed as vehicles. A vaginal insert may also contain the active ingredient in admixture with the common carriers, e.g. gelatin, adipic acid, sodium bicarbonate, lactose and analogs.

The compounds of the invention may also be administered in the form of their nontoxic, pharmaceutically acceptable acid addition salts. Such salts possess the same degree of activity as the free bases, from which they are readily prepared by reacting the base with an appropriate acid and, accordingly, are included within the scope of the invention. Representative of such salts are the mineral acid salts, such as, for instance, the hydrochloride, hydrobromide, sulfate and the like, and the organic acid salts, such as the succinate, benzoate, acetate, p-toluensulfonate, benzene sulfonate, maleate, tartrate, methanesulfonate, cycloheylsulfonate and the like.

The dosage of active ingredient employed for inhibiting reproduction may vary within wide limits, depending on the nature of the compound.

Generally, good results are obtained when the compounds of the above Formula I are administered in a single dosage from 0.1 to 25 mg/Kg intramuscularly or in a multiple dosage (for from 5 to 10 days) of 0.5 to 25 mg/kg orally or intravaginally. The dosage forms useful for this purpose generally contain from about 10 to about 600 mg of the active ingredient in admixture with a solid or liquid pharmaceutically acceptable carried or diluent. The following Examples illustrate the way of making the compounds of the invention and describe in detail some of them without limiting the purposes of the invention itself. In the Examples also the $\Delta \delta$ of each compound wherein R is other than hydrogen is reported. As stated above, this parameter is indicative of the position of the radical R on the two adjacent N-atoms of the triazole ring. Yields are calculated over the starting triazole; the $\Delta \delta$ values are expressed in ppm (parts per million).

EXAMPLE 1

1-Acetyl-3-(3-methoxyphenyl)-5-(2-methylphenyl)-1H-1,2,4-triazole

A solution of 0.8 g (0.003 mole) of 3-(3-methoxyphenyl)-5-(2-methylphenyl)-1H-1,2,4-triazole and 3 ml (0.00317 mole) of acetic anhydride was heated for two hours on a hot water bath. After evaporating the excess of anhydride by distillation under vacuum, the obtained residue was taken up with a mixture of diisopropyl ether and light petroleum. After standing overnight, a precipitate formed which was recovered by filtration. Yield: 0.72 g (78%) of the title compound M.p. 107°–110° C. $\Delta\delta = -0.26$.

EXAMPLES 2–7

The following compounds were prepared according to the same procedure outlined in Example 1.

EXAMPLE 2

1-Propionyl-3-(3-methoxyphenyl)-5-(2-methylphenyl)-1H-1,2,4-triazole from 3-(3-methoxyphenyl)-5-(2-methylphenyl)-1H-1,2,4-triazole and propionic anhydride. Yield 40% M.p. 84°–86° C. (from diethyl ether/light petroleum). $\Delta\delta = -0.26$.

EXAMPLE 3

1-(2,2-Dimethylpropionyl)-3-(3-methoxyphenyl)-5-(2-methylphenyl)-1H-1,2,4-triazole, from 3-(3-methoxyphenyl)-5-(2-methylphenyl)-1H-1,2,4-triazole and 2,2- dimethyl-propionic anhydride. Yield 20%. The compound is a not distillable oil. Δδ= −0.29.

EXAMPLE 4

1-Acetyl-3-(4-fluorophenyl)-5-(2-methylphenyl)-1H-1,2,4-triazole from 3-(4-fluorophenyl)-5-(2-methylphenyl)-1H-1,2,4-triazole and acetic anhydride. Yield 81% M.p. 118°-20° C. (from tert.-butyl-methyl ether). Δδ= −0.25.

EXAMPLE 5

1-Acetyl-5-(4-chloro-2-methylphenyl)-3-(3-methoxyphenyl)-1H-1,2,4-triazole from 5-(4-chloro-2-methylphenyl)-3-(3-methoxyphenyl)-1H-1,2,4-triazole and acetic anhydride. Yield 50%. M.p. 101°-103° C. (from diethyl ether/light petroleum). Δδ= −0.28.

EXAMPLE 6

1-Acetyl-5-(2-ethylphenyl)-3-(3-methoxyphenyl)-1H-1,2,4-triazole from 5-(2-ethylphenyl)-3-(3-methoxyphenyl)-1H-1,2,4-triazole and acetic anhydride. Yield 68%. M.p. 60°-64° C. (from light petroleum). Δδ= −0.31.

EXAMPLE 7

1-Acetyl-5-(2-acetoxymethylphenyl)-3-(3-methoxyphenyl)-1H-1,2,4-triazole, from 5-(2-hydroxymethylphenyl)-3-(3-methoxyphenyl)-1H-1,2,4-triazole and acetic anhydride. Yield 60%. M.p. 108°-10° C. (from tert.-butyl-methyl ether). Δδ= −0.37.

EXAMPLE 8

1-Carbethoxy-5-(2-ethylphenyl)-3-(3-methoxyphenyl)-1H-1,2,4-triazole

To a solution of 5.58 g (0.02 mole) of 5-(2-ethylphenyl)-3-(3-methoxyphenyl)-1H-1,2,4-triazole in 50 ml of anhydrous tetrahydrofuran, 0.66 g (0.02 mole) of an 80% oily suspension of sodium hydride were added. After the hydrogen development had ceased, a solution of 2 ml. (0.02 mole) of ethylchlorocarbonate in 20 ml of anhydrous tetrahydrofuran was added dropwise under stirring and the temperature was kept at 15°-20° C. Stirring was continued for 2,5 hours then, after adding 200 ml of anhydrous diethyl ether, the reaction mixture was filtered under vacuum and the filtrate brought to pH 3 by means of hydrogen chloride. The little amount of unreacted starting triazole which precipitated as the hydrochloride was filtered under vacuum, the filtrate was added with solid sodium bicarbonate and the resulting mixture stirred five minutes. After filtering the inorganic salts, the solution was concentrated to about 30 ml and kept overnight at about −10° C. 3.65 Grams of the compound of the title were obtained. M.p. 80°-82° C. Δδ= −0.30.

EXAMPLES 9-12

The following compounds were prepared according to the same procedure of the foregoing Example.

EXAMPLE 9

1-Carbomethoxy-5-(2-ethylphenyl)-3-(3-methoxyphenyl)-1H-1,2,4-triazole, from 5-(2-ethylphenyl)-3-(3-methoxyphenyl)-1H-1,2,4-triazole and methyl chlorocarbonate. Yield 50%. M.p. 95°-97° C. (from light petroleum). Δδ= −0.28.

EXAMPLE 10

1-Carbethoxy-3-(3-methoxyphenyl)-5-(2-methylphenyl)-b 1H-1,2,4-triazole, from 3-(3-methoxyphenyl)-5-(2-methylphenyl)-1H-1,2,4-triazole and ethyl chlorocarbonate. Yield 60%. M.p. 77°-81° C. (from light petroleum). Δδ= −0.23.

EXAMPLE 11

1-Benzoyl-3-(3-methoxyphenyl)-5-(2-methylphenyl)-1H-1,2,4-triazole, from 3-(3-methoxyphenyl)-5-(2-methylphenyl)-1H-1,2,4-triazole and benzoyl chloride. Yield 40%. M.p. 62°-65° C. (from diethyl ether/light petroleum). Δδ= −0.18.

EXAMPLE 12

1-Diethylcarbamoyl-3-(3-methoxyphenyl)-5-(4-methoxy-2-methylphenyl)-1H-1,2,4-triazole, from 3-(3-methoxyphenyl)-5-(4-methoxy-2-methylphenyl)-1H-1,2,4-triazole and diethylcarbamoyl chloride. Yield 50% M.p. 58°-62° C. (from diethyl ether/light petroleum). Δδ= −0.20.

EXAMPLE 13

3-(3-Methoxyphenyl)-5-(2-methylphenyl)-1-phenylcarbamoyl-1H-1,2,4-triazole

A solution of 0.53 g (0.002 mole) of 3-(3-methoxyphenyl)-5-(2-methylphenyl)-1H-1,2,4-triazole and 0.22 ml. (0.002 mole) of phenylisocyanate in 5 ml of acetonitrile was strred for 7 hours at room temperature and, subsequently, it was left standing overnight. The solvent was evaporated off and the obtained residue was first taken up with hexane, then, after separating the liquid and the solid phase by decantation, it was recrystallized from acetonitrile. Yield: 0.25 g of the title compound. M.p. 123°-125° C. Δδ= −0.18.

EXAMPLES 14-20

The following compounds were prepared according to the same procedure outlined in Example 13.

EXAMPLE 14

1-Ethylcarbamoyl-3-(3-methoxyphenyl)-5-(2-methylphenyl)-1H-1,2,4-triazole, from 3-(3-methoxyphenyl)-5-(2-methylphenyl)-1H-1,2,4-triazole and ethylisocyanate. Yield 80%. M.p. 117°-19° C. (from diethyl ether/light petroleum). Δδ= −0.22.

EXAMPLE 15

5-(2-Ethylphenyl)-3-(3-methoxyphenyl)-1-methylcarbamoyl-1H-1,2,4-triazole, from 5-(2-ethylphenyl)-3-(3-methoxyphenyl)1H-1,2,4-triazole and methylisocyanate. Yield 60%. M.p. 107°-8° C. (from diethyl ether/light petroleum). Δδ= −0.31.

EXAMPLE 16

5-(2-Ethylphenyl)-3-(3-methoxyphenyl-1-phenylcarbamoyl-1H-1,2,4-triazole, from 5-(2-ethylphenyl)-3-(3-methoxyphenyl)-1H-1,2,4-triazole and phenyl isocyanate. Yield 76%. M.p. 99°-100° C. (from diethyl ether). Δδ= −0.20.

EXAMPLE 17

5-(2-Ethylphenyl)-3-(3-methoxyphenyl)-1-(4-methoxyphenyl carbamoyl)-1H-1,2,4-triazole, from 5-(2-ethylphenyl)-3-(3-methoxyphenyl)-1H-1,2,4-triazole and 4- methoxyphenyl isocyanate. Yield 57%. M.p. 114°–15° C. (from diethyl ether). Δδ= −0.20.

EXAMPLE 18

1-(2-Chlorophenylcarbamoyl)-5-(2-ethylphenyl-3-(3-methoxyphenyl)-1H-1,2,4-triazole, from 5-(2-ethylphenyl)-3-(3-methoxyphenyl)-1H-1,2,4-triazole and 2-chlorophenyl isocyanate. Yield 87% M.p. 127°–29° C. (from acetonitrile). Δδ= −0.20.

EXAMPLE 19

1-(4-Chlorophenylcarbamoyl)-5-(2-ethylphenyl)-3-(3-methoxyphenyl)-1H-1,2,4-triazole, from 5-(2-ethylphenyl)-3-(3-methoxyphenyl)-1H-1,2,4-triazole and 4-chlorophneyl isocyanate. Yield 90%. M.p. 133°–35° C. (from acetonitrile). Δδ= −0.29.

EXAMPLE 20

5-(2-Ethylphenyl)-3-(3-methoxyphenyl)-1-(4-nitrophenyl)carbamoyl-1H-1,2,4-triazole, from 5-(2-ethylphenyl)-3-(3-methoxyphenyl)-1H-1,2,4-triazole and 4-nitrophenyl isocyanate. Yield 40% M.p. 141°–42° C. (from acetonitrile). Δδ= −0.18.

EXAMPLE 21

5-(2-Ethylphenyl)-3-(3-methoxyphenyl)-1-(4-methylphenylcarbamoyl)-1H-1,2,4-triazole and 3-(2-ethylphenyl)-5-(3-methoxyphenyl)-1-(4-methylphenylcarbamoyl)-1H-1,2,4-triazole.

(a) To a solution of 5 g (0.018 mole) of 5-(2-ethylphenyl)-3-(3-methoxyphenyl)-1H-1,2,4-triazole in 50 ml of anhydrous acetonitrile, 2,25 ml (0.018 mole) of 4-methylphenyl isocyanate were added. The resulting mixture was kept in the darkness for 18 hours, then the solid which formed was recovered by filtration and the mother liquors were brought to dryness under vacuum at room temperature. The obtained residue was taken up with 20 ml of diethyl ether, the mixture was filtered and the solid on the filter was collected with the solid deriving from the first filtration. 5.9 Grams (80%) of 5-(2-ethylphenyl)-3-(3-methoxyphenyl)-1-(4-methylphenylcarbamoyl)-1H-1,2,4-triazole were obtained. M.p. 141°–42° C. (from acetonitrile). Δδ= −0.24.

(b) From the ethereal mother liquors deriving from the second filtration a solid product separated which was collected by filtration under vacuum. 0.53 g (7%) of 3-(2-ethylphenyl)-5-(3-methoxyphenyl)-1-(4-methylphenylcarbamoyl)-1H-1,2,4-triazole. M.p. 95°–96° C. (from diethylether). Δδ= +0.30.

EXAMPLES 22–23

The following pair of isomers were obtained according to the same procedure of the above Example.

EXAMPLE 22

3-(3-Methoxyphenyl)-5-(2-methylphenyl)-1-(4-methylphenylcarbamoyl)-1H-1,2,4-triazole and 5-(3-methoxyphenyl)-3-(2-methylphenyl)-1-(4-methylphenylcarbamoyl)-1H-1,2,4-triazole, from 3-(3-methoxyphenyl)-5-(2-methylphenyl)-1H-1,2,4-triazole and 4-methylphenyl isocyanate.

(a) Yield of 3-(3-methoxyphenyl)-5-(2-methylphenyl)-1-(4-methylphenylcarbamoyl)-1H-1,2,4-triazole: 75% M.p. 140°–41° C. (from acetonitrile). Δδ= −0.16.

(b) Yield of 5-(3-methoxyphenyl)-3-(2-methylphenyl)-1-(4-methylphenylcarbamoyl)-1H-1,2,4-triazole: 8% M.p. 92°–94° C. (from diethyl ether). Δδ= +0.28.

EXAMPLE 23

3-(4-Chlorophenyl)-5-(2-methylphenyl)-1-(4-methylphenylcarbamoyl)-1H-1,2,4-triazole and 5-(4-chlorophenyl)-3-(2-methylphenyl)-1-(4-methylphenylcarbamoyl)-1H-1,2,4-triazole, from 3-(4-chlorophenyl)-5-(2-methylphenyl)-1H-1,2,4-triazole and 4-methylphenyl-isocyanate.

(a) Yield of 3-(4-chlorophenyl)-5-(2-methylphenyl)-1-(4-methylphenylcarbamoyl)-1H-1,2,4-triazole: 20% M.p. 134°–35° C. (from acetonitrile). Δδ= −0.23.

(b) Yield of 5-(4-chlorophenyl)-3-(2-methylphenyl)-1-(4-methylphenylcarbamoyl)-1H-1,2,4-triazole: 25% M.p. 132°–34° C. (from acetonitrile). Δδ= +0.22.

EXAMPLE 24

5-(2-Acetoxymethylphenyl)-3-(3-methoxyphenyl)-1H-1,2,4-triazole

To a solution of 0.44 g (0.0012 mole) of the compound of Example 7 in 10 ml of dioxane, 10 ml of a 4% solution of sodium bicarbonate (0.0024 mole) were added at room temperature. A gentle stirring was applied for about 3 hours, then the mixture was left standing, again at room temperature, for 15 hours. After removing the solvent by distillation under vacuum a residue was obtained, which was extracted three times with diethyl ether. After drying over sodium sulfate and evaporating the solvent a residue was obtained which was recrystallized from hexane/diethyl ether. Yield 0.254 g (65%), M.p. 83°–87° C.

EXAMPLE 25

5-(2-Ethylphenyl)-3-(3-methoxyphenyl)-1-(4-methylphenylcarbamoyl)-1H-1,2,4-triazole A 10 ml flask containing 0.1 g (0.000248 mole) of 3-(2-ethylphenyl)-5-(3-methoxyphenyl)-1-(4-methylphenylcarbamoyl)-1H-1,2,4-triazole (Δδ= +0.30) under an argon atmosphere was poured into an oil bath at a temperature of 100° C. The product melted and became again solid in about 1 minute. After cooling, the obtained product was triturated with a small amount of diethyl ether and recovered by filtration under vacuum. Yield: 0.095 g (95%) of the title compound having Δδ= −0.24. M.p. 141°–42° C. (from acetonitrile).

EXAMPLE 26

Preparation of 4-phenyl-2-(2-methylphenyl)-1H-imidazole (compound of formula III)

To a solution of 6.1 g (0.0455 mole) of 2-methylbenzamidine in 25 ml of chloroform 3.6 g (0.018 mole) of α-bromoacetophenone were added and the resulting mixture was refluxed for four hours. After cooling and adding 50 ml of chloroform the reaction mixture was first washed with diluted ammonia and then with water and subsequently dried over sodium sulfate. The sodium sulfate was removed by filtration and the filtrate was chromatographed through silica gel by eluting with mixtures of $CHCl_3/CH_3COOC_2H_5$ containing up to a maximum of 4% (in volume) of $CH_3COOC_2H_5$. The fractions eluted with $CH_3Cl_3/CH_3COOC_2H_5=9/1$ (v/v) were collected, the solvent was evaporated off and the residue was crystallized from diethylether/light petroleum. Yield 1.95 g (46.3%) of the title compound M.p. 145°–46° C.

N.M.R. spectrum (solvent: CDCl$_3$; chemical shifts=δ units); 2,42 (s, 3H, CH$_3$ (tolylic protons); 7.1–7.7 (m,10, H, aromatic H+NH); 7.20 (s, 1H, CH=).

s=singlet
m=multiplet

EXAMPLE 27

Preparation of
1-acetyl-4-phenyl-2-(2-methylphenyl)-1H-imidazole
(compound of formula IV)

0.702 g (0.003 mole) of the compound of Example 26 and 3 ml (0.00317 mole) of acetic anhydride were heated on an oil bath at 95° C. for 2 hours, then the excess of acetic anhydride was distilled under vacuum. The obtained residue was crystallized from tert-butyl-methyl ether/light petroleum. Yield 0.69 g (83%) of the title compound M.p. 102°–4° C.

N.M.R. spectrum (solvent=CDCl$_3$; chemical shifts=δ units): 2.15 (s, 3H, COCH$_3$); 2.24 (s, 3H, CH$_3$, tolylic protons); 7.1–7.9 (m, 9H, aromatic H); 7.94 (s, 1H, CH=). The introduction of the acetyl group as shown in formula IV has caused a negative Δδ of the tolylic protons.

EXAMPLE 28

A vial for injectable use is prepared from

| | |
|---|---|
| 1-Acetyl-3-(methoxyphenyl)-5-(2-methyl-phenyl-1H—1,2,4-triazole | 30 mg |
| Benzyl benzoate | 220 mg |
| Sesame oil q.s. to | 2 ml |

EXAMPLE 29

A vial for injectable use is prepared from

| | |
|---|---|
| 1-Acetyl-5-(2-ethylphenyl)-3-(3-methoxy-phenyl)-1H—1,2,4-triazole | 30 mg |
| Benzyl alcohol | 100 mg |
| Peanut oil q.s. to | 2 ml |

EXAMPLE 30

A vial for injectable use is prepared from

| | |
|---|---|
| 3-(3-Methoxyphenyl)-5-(2-methylphenyl)-1-phenylcarbamoyl-1H—1,2,4-triazole | 20 mg |
| Benzyl alcohol | 80 mg |
| Castor oil q.s. to | 2 ml |

EXAMPLE 31

A sugar coated tablet is prepared from

| | |
|---|---|
| 1-(2-Chlorophenylcarbamoyl)-5-(2-ethylphenyl)-3-(3-methoxyphenyl)-1H—1,2,4-triazole | 100 mg |
| Sodium carboxymethylcellulose | 5 mg |
| Magnesium stearate | 5 mg |
| Gelatin | 10 mg |
| Starch | 10 mg |
| Saccharose | 25 mg | gum arabic, lactose, titan dioxide, aluminium lac according to conventional procedures.

EXAMPLE 32

A capsule is prepare from

| | |
|---|---|
| 3-(2-Ethylphenyl)-5-(3-methoxyphenyl)-1-(4-methylphenylcarbamoyl)-1H—1,2,4-triazole | 60 mg |
| Talc | 5 mg |
| Lactose | 5 mg |
| Sodium carboxymethylcellulose | 5 mg |
| Starch q.s. to | 150 mg |

EXAMPLE 33

A tablet is prepared from

| | |
|---|---|
| 5-(2-Acethoxymethylphenyl)-3-(3-methoxy-phenyl)-1H—1,2,4-triazole | 100 mg |
| Levilite | 100 mg |
| Starch | 80 mg |
| Magnesium stearate | 10 mg |

According to the above illustrated procedures it is possible to prepare the compounds of formula I listed in the Table below. The expressions -3(5)- and -5(3)- before each substituent corresponding to

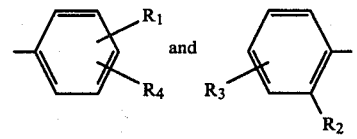

indicate that compounds can be prepared wherein R, when it represents R$_5$ —CO or R$_6$ —SO$_2$, is located on one or the other of the two adjacent nitrogen atoms and, consequently, the two above phenyl radicals may be either at the 3- or at the 5-position.

-1H-1,2,4-triazole

1-Butyryl-3(5)-(3-methoxyphenyl)-5(3)-(2-methylphenyl)

1-Acetyl-3(5)-(3-ethoxyphenyl)-5(3)-(2-methylphenyl)

3(5)-(3-Ethoxyphenyl)-5(3)-(2-methylphenyl)-1-propionyl

1-Butyryl-5(3)-(2-ethylphenyl)-3(5)-(3-methoxyphenyl)

1-Acetyl-3(5)-(3-allyloxyphenyl)-5(3)-(2-ethylphenyl)

3(5)-(3-Allyloxyphenyl)-5(3)-(2-ethylphenyl)-1-propionyl

1-Acetyl-5(3)-(2-ethylphenyl)-3(5)-(3-fluorophenyl)

5(3)-(2-Ethylphenyl)-3(5)-(3-fluorophenyl)-1-propionyl

1-Acetyl-5(3)-(2-ethylphenyl)-3(5)-(3,4-methylenedioxyphenyl)

5(3)-(2-Ethylphenyl)-3(5)-(3,4-methylenedioxyphenyl)-1-propionyl)

1-Acetyl-5(3)-(2,4-dimethylphenyl)-3(5)-(3-methoxyphenyl)

5(3)-(2,4-Dimethylphenyl)-3(5)-(3-methoxyphenyl)-1-propionyl

5(3)-(4-Chloro-2-methylphenyl)-3(5)-(3-methoxyphenyl)-1-propionyl

1-Acetyl-5(3)-(4-methoxy-2-methylphenyl)-3(5)-(3-methoxyphenyl)

5(3)-(4-Methoxy-2-methylphenyl)-3(5)-(3-methoxyphenyl)-1-propionyl

1-Acetyl-3(5)-(3-ethoxyphenyl)-5(3)-(2-ethylphenyl)

3(5)-(3-Ethoxyphenyl)-5(3)-(2-ethylphenyl)-1-propionyl
1-Acetyl-5(3)-(2-ethylphenyl)-3(5)-(3,4-dimethoxyphenyl)
5(3)-(2-Ethylphenyl)-3(5)-(3,4-dimethoxyphenyl)-1-propionyl
1-Acetyl-5(3)-(2-formylphenyl)-3(5)-(3-methoxyphenyl)
5(3)-(2-Formylphenyl)-3(5)-(3-methoxyphenyl)-1-propionyl
1-Benzoyl-3(5)-(3-ethoxyphenyl)-5(3)-(2-methylphenyl)
1-Benzoyl-5(3)-(2-ethylphenyl)-3(5)-(3-methoxyphenyl)
1-Benzoyl-5(3)-(2-ethylphenyl)-3(5)-(3-fluorophenyl)
1-Benzoyl-5(3)-(2-ethylphenyl)-3(5)-(3,4-methylenedioxyhenyl)
1-Benzoyl-5(3)-(2,4-dimethylphenyl)-3(5)-(3-methoxyphenyl)
1-Benzoyl-5(3)-(4-chloro-2-methylphenyl)-3(5)-(3-methoxyphenyl)
1-Benzoyl-5(3)-(4-methoxy-2-methylphenyl)-3(5)-(3-methoxyphenyl)
1-Benzoyl-3(5)-(3-ethoxyphenyl)-5(3)-(2-ethylphenyl)
1-Benzoyl-5(3)-(2-ethylphenyl)-3(5)-(3,4-dimethoxyphenyl)
1-Benzoyl-5(3)-(2-formylphenyl)-3(5)-(3-methoxyphenyl)
1-(4-Chlorobenzoyl)-3(5)-(3-methoxyphenyl)-5(3)-(2-methylphenyl)
1-(4-Fluorobenzoyl)-3(5)-(3-methoxyphenyl)-5(3)-(2-methylphenyl)
1-(4-Chlorobenzoyl)-5(3)-(2-ethylphenyl)-3(5)-(3-methoxyphenyl)
5(3)-(2-Ethylphenyl)-1-(4-fluorobenzoyl)-3(5)-(3-methoxyphenoyl)
1-(3-Ethylbenzoyl)-3(5)-(3-methoxyphenyl-5(3)-(2-methylphenyl)
1-(3-Methoxybenzoyl)-3(5)-(3-methoxyphenyl)-5(3)-(2-methylphenyl)
5(3)-(2-Ethylphenyl)-1-(3-methoxybenzoyl)-3(5)-(3-methoxyphenyl)
1-(3-Ethoxybenzoyl)-3(5)-(3-methoxyphenyl)-5(3)-(2-methylphenyl)
1-(3-Ethoxybenzoyl)-5(3)-(2-ethylphenyl)-3(5)-(3-methoxyphenyl)
3(5)-(3-Methoxyphenyl)-5(3)-(2-Methylphenyl)-1-(4-trifluoromethylbenzoyl)
5(3)-(2-Ethylphenyl)-3(5)-(3-methoxyphenyl)-1-(4-trifluoromethylbenzoyl)
3(5)-(3-Methoxyphenyl)-1-(3,4-methylenedioxybenzoyl)-5(3)-(2-methylphenyl)
1-(4-Dimethylaminobenzoyl)-3(5)-(3-methoxyphenyl)-5(3)-(2-methylphenyl)
1-(3-Dimethylaminobenzoyl)-5(3)-(2-ethylphenyl)-3(5)-(3-methoxyphenyl)
1-Carbomethoxy-5(3)-(2-ethylphenyl)-3(5)-(3-fluorophenyl)
1-Carbethoxy-5(3)-(2-ethylphenyl)-3(5)-(3,4-methylenedioxyphenyl)
1-Carbopropoxy-5(3)-(2,4-dimethylphenyl)-3(5)-(3-methoxyphenyl)
1-Carbethoxy-5(3)-(4-chloro-2-methylphenyl)-3(5)-(3-methoxyphenyl)
1-Carbethoxy-5(3)-(4-methoxy-2-methylphenyl)-3(5)-(3-methoxyphenyl)
1-Carbethoxy-3(5)-(3-ethoxyphenyl)-5(3)-(2-ethylphenyl)
1-Carbethoxy-5(3)-(2-ethylphenyl)-3(5)-(3,4-dimethoxyphenyl)
1-Carbethoxy-5(3)-(2-formylphenyl)-3(5)(3-methoxyphenyl)
3(5)-(3-Methoxyphenyl)-5(3)-(2-methylphenyl)-1-phenacetyl
1-Carbamoyl-3(5)-(3-methoxyphenyl)-5(3)-(2-methylphenyl)
1-Methylcarbamoyl-3(5)-(3-ethoxyphenyl)-5(3)-(2-methylphenyl)
1-Ethylcarbamoyl-5(3)-(2-ethylphenyl)-3(5)-(3-methoxyphenyl)
1-(i-Propylcarbamoyl)-5(3)-(2-ethylphenyl)-3(5)-(3-fluorophenyl)
1-Ethylcarbamoyl-5(3)-(2-ethylphenyl)-3(5)-(3,4-methylenedioxyphenyl)
1-Ethylcarbamoyl-5(3)-(4-chloro-2-methylphenyl)-3(5)-(3-methoxyphenyl)
1-Butylcarbamoyl-5(3)-(4-methoxy-2-methylphenyl)-3(5)-(3-methoxyphenyl)
1-Ethylcarbamoyl-5(3)-(2-ethylphenyl)-3(5)-(3,4-dimethoxyphenyl)
1-Diethylcarbamoyl-3(5)-(3-methoxyphenyl)-5(3)-(2-methylphenyl)
1-Diethylcarbamoyl-3(5)-(3-ethoxyphenyl)-5(3)-(2-methylphenyl)
1-Diethylcarbamoyl-5(3)-(2-ethylphenyl)-3(5)-(3-methoxyphenyl)
3(5)-(3-Ethoxyphenyl)-5(3)-(2-methylphenyl)-1-phenylcarbamoyl
5(3)-(2-Ethylphenyl)-3(5)-(3-fluorophenyl)-1-phenylcarbamoyl
5(3)-(2-Ethylphenyl)-3(5)-(3,4-methylenedioxyphenyl)-1-phenylcarbamoyl
5(3)-(2,4-Dimethylphenyl)-3(5)-(3-methoxyphenyl)-1-phenylcarbamoyl
5(3)-(4-Chloro-2-methylphenyl)-3(5)-(3-methoxyphenyl)-1-phenylcarbamoyl
5(3)-(4-Methoxy-2-methylphenyl)-3(5)-(3-methoxyphenyl)-1-phenylcarbamoyl
3(5)-(3-Ethoxyphenyl)-5(3)-(2-ethylphenyl)-1-phenylcarbamoyl
5(3)-(2-Ethylphenyl)-3(5)-(3,4-dimethoxyphenyl)-1-phenylcarbamoyl
5(3)-(2-Formylphenyl)-3(5)-(3-methoxyphenyl)-1-phenylcarbamoyl
1-(4-Chloro-phenylcarbamoyl)-3(5)-(3-methoxyphenyl)-5(3)-(2-methylphenyl
1-(4-Fluoro-phenylcarbamoyl)-3(5)-(3-methoxyphenyl)-5(3)-(2-methylphenyl)
1-(3-Chloro-phenylcarbamoyl)-5(3)-(2-ethylphenyl)-3(5)-(3-methoxyphenyl)
5(3)-(2-Ethylphenyl)-1-(4-fluoro-phenylcarbamoyl)-3(5)-(3-methoxyphenyl)
1-(3-Methyl-phenylcarbamoyl)-3(5)-(3-methoxyphenyl)-5(3)-(2-methylphenyl)
3(5)-(3-Methoxyphenyl)-1-(3-methoxy-phenylcarbamoyl)-5(3)-(2-methylphenyl)
1-(4-Methoxy-phenylcarbamoyl)-3(5)-(3-methoxyphenyl)-5(3)-(2-methylphenyl)
5(3)-(2-Ethylphenyl)-3(5)-(3-methoxyphenyl)-1-(2-methoxyphenylcarbamoyl)
5(3)-(2-Ethylphenyl)-3(5)-(3-methoxyphenyl)-1-(3-methoxyphenylcarbamoyl)
1-(4-Dimethylamino-phenylcarbamoyl)-3(5)-(3-methoxyphenyl)-5(3)-(2-methylphenyl)
1-(4-Dimethylamino-phenylcarbamoyl)-5(3)-(2-ethylphenyl)-3(5)-(3-methoxyphenyl)
3(5)-(3-Methoxyphenyl)-5(3)-(2-methylphenyl)-1-(3,4-methylenedioxy-phenylcarbamoyl)

3(5)-(3-Methoxyphenyl)-5(3)-(2-methylphenyl)-1-(3-trifluoromethylphenylcarbamoyl)

5(3)-(2-Ethylphenyl)-3(5)-(3-methoxyphenyl)-1-(2-trifluoromethylphenylcarbamoyl)

3(5)-(3-Methoxyphenyl)-5(3)-(2-methylphenyl)-1-methylsulfonyl

5(3)-(2-Ethylphenyl)-1-ethylsulfonyl-3(5)-(3-methoxyphenyl)

1-Benzenesulfonyl-3(5)-(3-methoxyphenyl)-5(3)-(2-methylphenyl)

1-Benzenesulfonyl-5(3)-(2-ethylphenyl)-3(5)-(3-methoxyphenyl)

3(5)-(3-Methoxyphenyl)-5(3)-(2-methylphenyl)-1-toluenesulfonyl

5(3)-(2-Ethylphenyl)-3(5)-(3-methoxyphenyl)-1-toluenesulfonyl

5(3)-(2-Ethylphenyl)-3(5)-(3-methoxyphenyl)-1-phenacylsulfonyl

3(5)-(3-Methoxyphenyl)-1-propionyl-5(3)-(2-propionyloxymethylphenyl)

1-Benzoyl-5(3)-(2-benzoyloxymethylphenyl)-3(5)-(3-methoxyphenyl)

1-Carbamoyl-5(3)-(2-carbamoyloxymethylphenyl)-3(5)-(3-methoxyphenyl)

1-Ethylcarbamoyl-5(3)-(2-ethylcarbamoyloxymethylphenyl)-3(5)-(3-methoxyphenyl)

1-Diethylcarbamoyl-5(3)-(2-diethylcarbamoyloxymethylphenyl)-3(5)-(3-methoxyphenyl)

3(5)-(3-Methoxyphenyl)-1-phenylcarbamoyl-5(3)-(2-phenylcarbamoyloxymethyl-phenyl)

5-(2-Benzoyloxymethylphenyl)-3(3-methoxyphenyl)

3-(3-Methoxyphenyl)-5-(2-propionyloxymethylphenyl)

5-(2-Carbamoyloxymethylphenyl)-3-(3-methoxyphenyl)

5-(2-Ethylcarbamoyloxymethyl-phenyl)-3-(3-methoxyphenyl)

5-(2-Diethylcarbamoyloxymethyl-phenyl)-3-(3-methoxyphenyl)

3-(3-Methoxyphenyl)-5-(2-phenylcarbamoyloxymethyl-phenyl)

1-Trifluoroacetyl-3-(3-methoxyphenyl)-5-(2-methylphenyl)

1-Trifluoroacetyl-3-(3-methoxyphenyl)-5-(2-ethylphenyl)

1-(2-Butenoyl)-3-(methoxyphenyl)-5-(2-methylphenyl)

1-(2-Acryloyl)-3-(3-methoxyphenyl)-5-(2-ethylphenyl)

1-Dichloroacetyl-3-(3-methoxypyenyl)-5-(2-ethylphenyl)

1-Chloroacetyl-3-(3-methoxyphenyl)-5-(2-methylphenyl)

1-Trifluoroacetyl-3-(3-methoxyphenyl)-5-[2-(trifluoroacetoxy)methylphenyl]

1-Cinnamoyl-3-(3-methoxyphenyl)-5-(2-ethylphenyl)

1-(2-Propiolyl)-3-(3-methoxyphenyl)-5-(2-ethylphenyl)

1-Cinnamoyl-3-(3-methoxyphenyl)-5-(2-methylphenyl)

1-Benzyloxycarbonyl-3-(3-methoxyphenyl)-5-(2-ethylphenyl)

1-Benzyloxycarbonyl-3-(3-methoxyphenyl)-5-(2-methylphenyl)

5-[2-(Benzyloxycarbonyloxy)methylphenyl]-1-benzyloxycarbonyl-3-(3-methoxyphenyl)

1-Cinnamoyl-3-(3-methoxyphenyl)-5-[2-(cinnamoyloxy)methylphenyl]

3-(3-Methoxyphenyl)-5-[2-(trifluoroacetoxy)methylphenyl]

3-(3-Methoxyphenyl)-5-[2-(benzyloxycarbonyloxy)methylphenyl]

3-(3-Methoxyphenyl)-5-[2-(cinnamoyloxy)methylphenyl]

Preparation of the starting 3,5-disubstituted 1H-1,2,4-triazoles (A) 3-(3-Methoxyphenyl)-5-(2-methylphenyl)-1H-1,2,4-triazole A mixture of 3.0 g (0.02 mole) of the hydrazide of 2-methyl-benzoic acid and 4.83 g (0.027 mole) of 3-methoxybenzimidic acid ethyl ester was heated on an oil bath under stirring for about 20 hours, keeping the temperature of the oil bath at about 125° C. After cooling, the reaction mass was taken up with 100 ml of diethyl ether and the obtained ether solution was first extracted with 50 ml of 5% aqueous sodium hydroxide and then twice with 30 ml of water. The water and alkaline extracts were combined together, treated with charcoal to remove any impurity and filtered on celite. The filtrate was brought to pH 7 by adding under stirring 10% aqueous hydrochloric acid whereby an oily substance separated which was extracted with diethyl ether. After drying over sodium sulfate, the ether was evaporated off in vacuo and the obtained residue was recrystallized from diisopropyl ether/hexane. Yield 3.15 g M.p. 100°-2° C.

The following starting 3,5-disubstituted 1H-1,2,4-triazoles were prepared according to the same procedure of the foregoing Example.

(B) 3-(4-Fluorophenyl)-5-(2-methylphenyl)-1H-1,2,4-triazole M.p. 119°-21° C. (from hexane/diisopropyl ether)

(C) 3-(4-Chlorophenyl)-5-(2-methylphenyl)-1H-1,2,4-triazole M.p. 150°-51° C. (from diisopropyl ether)

(D) 5-(2-Ethylphenyl)-3-(3-methoxyphenyl)-1H-1,2,4-triazole M.p. 174°-77° C. (from ethanol/diethyl ether)

(E) 5-(4-Methoxy-2-methylphenyl)-3-(3-methoxyphenyl)-1H-1,2,4-triazole M.p. 121°-22° C. (from ethanol/diethylether)

(F) 5-(4-Chloro-2-methylphenyl)-3-(3-methoxyphenyl)-1H-1,2,4-triazole. M.p. 137°-38° C. (from ethanol/diethylether).

We claim:

1. A compound represented by the formula

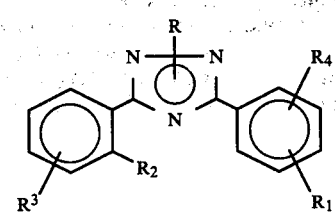

wherein
R is located on one of the two adjacent nitrogen atoms and represents a member of the group consisting of
(a) a group $R_5$—CO wherein $R_5$ is selected from $(C_{1-4})$alkyl; $(C_{2-4})$alkenyl; $(C_{2-4})$alkynyl; phenyl; phenyl substituted by one to three groups independently selected from halo, $(C_{1-4})$alkyl, $(C_{1-4})$alkoxy, trifluoromethyl, cyano, nitro, amino, di-$(C_{1-4})$alkylamino, $(C_{2-4})$alkanoylamino and methylenedioxy; cinnamyl; benzyl; amino, $(C_{1-4})$alkylamino; phenylamino; phenylamino wherein the phenyl ring may be substituted by one to three groups independently selected from halo, $(C_{1-4})$alkyl, $(C_{1-4})$alkoxy, trifluoromethyl, cyano, nitro, amino, di-$(C_{1-4})$alkylamino, $(C_{2-4})$alkanoylamino and methylenedioxy; halo$(C_{1-4})$alkyl; $(C_{1-4})$alkoxy and benzyloxy; or (b) a group $R_6$—$SO_2$ wherein $R_6$ may represent $(C_{1-4})$alkyl; phenyl; phenyl substituted by a radical selected from $(C_{1-4})$alkyl and $(C_{1-4})$alkoxy; or phenacyl;

$R_1$ is selected from hydrogen, $(C_{1-4})$alkyl, $(C_{1-4})$alkoxy, allyloxy, propargyloxy, trifluoromethyl, phenyl, halo and dimethylamino;

$R_2$ may represent a $(C_{1-4})$alkyl radical;

$R_3$ and $R_4$ are independently selected from hydrogen, halo, $(C_{1-4})$alkyl and $(C_{1-4})$alkoxy;

$R_1$ and $R_4$ taken together may also represent a methylenedioxy group; or a salt thereof with a pharmaceutically acceptable acid.

2. A compound as defined in claim 1, wherein

R is located on one of the two adjacent nitrogen atoms and represents the group $R_5$—CO in which $R_5$ is selected from $(C_{1-4})$alkyl; phenyl; phenyl substituted by a radical selected from halo, $(C_{1-4})$alkyl, $(C_{1-4})$alkoxy and nitro; amino; $(C_{1-4})$alkylamino; phenylamino; phenylamino wherein the phenyl ring is substituted by a group selected from halo, $(C_{1-4})$alkyl, $(C_{1-4})$alkoxy and nitro; and $(C_{1-4})$alkoxy;

$R_1$ is selected from, $(C_{1-4})$alkoxy, allyloxy, propargyloxy and halo;

$R_2$ represents a $(C_{1-4})$alkyl radical;

$R_3$ and $R_4$ are independently selected from hydrogen, halo and $(C_{1-4})$alkoxy; or a salt thereof with a pharmaceutically acceptable acid.

3. A compound as defined in claim 1, wherein

R may be located on one of the two adjacent nitrogen atoms and represents the group $R_5$—CO in which $R_5$ is selected from $(C_{1-4})$alkyl; phenyl; amino; $(C_{1-4})$alkylamino; phenylamino; phenylamino wherein the phenyl ring is substituted by a group selected from halo, $(C_{1-4})$alkyl, $(C_{1-4})$alkoxy and nitro;

$R_1$ represents halo or $(C_{1-4})$alkoxy;

$R_2$ is a $(C_{1-4})$alkyl radical;

$R_3$ and $R_4$ are independently selected from hydrogen, halo and $(C_{1-4})$alkoxy; or a salt thereof with a pharmaceutically acceptable acid.

4. A compound as defined in claim 1, wherein

R may be located on one of the two adjacent nitrogen atoms and represents the group $R_5$—CO wherein $R_5$ is selected from $(C_{1-4})$alkyl; phenyl; amino; methylamino; ethylamino; phenylamino; phenylamino in which the phenyl ring is substituted by a group selected from methyl, ethyl, methoxy, ethoxy, fluoro, chloro and nitro; and $(C_{1-4})$alkoxy;

$R_1$ represents chloro, fluoro, methoxy or ethoxy;

$R_2$ represents a $(C_{1-4})$alkyl radical;

$R_3$ may be hydrogen, fluoro, chloro, methoxy or ethoxy; and $R_4$ is hydrogen; or a salt thereof with a pharmaceutically acceptable acid.

5. 1-Acetyl-3-(3-methoxyphenyl)-5-(2-methylphenyl)-1H-1,2,4-triazole.

6. 1-Acetyl-5-(2-ethylphenyl)-3-(3-methoxyphenyl)-1H-1,2,4-triazole.

7. 3-(3-Methoxyphenyl)-5-(2-methylphenyl)-1-phenylcarbamoyl-1H-1,2,4-triazole.

8. 1-(2-Chlorophenylcarbamoyl)-5-(2-ethylphenyl)-3-(3-methoxyphenyl-1H-1,2,4-triazole.

9. 3-(2-Ethylphenyl)-5-(3-methoxyphenyl)-1-(4-methylphenylcarbamoyl)-1H-1,2,4-triazole.

10. An anti-reproductive pharmaceutical composition containing from about 10 to about 600 mg of a compound of formula

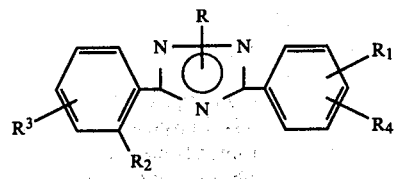

wherein R, $R_1$, $R_2$, $R_3$ and $R_4$ are defined as in claim 1, in admixture with an acceptable pharmaceuticaal carrier.

11. A method for preventing reproduction in warm-blooded animals, which comprises administering to the animal a dosage from about 0.1 to about 25 mg/kg of body weight of a compound of formula

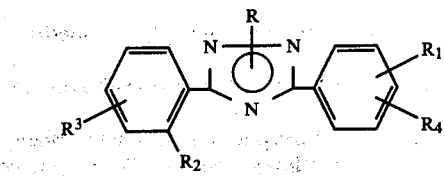

wherein R, $R_1$, $R_2$, $R_3$ and $R_4$ are defined as in claim 1.

* * * * *